United States Patent
Keller et al.

(10) Patent No.: US 11,074,833 B2
(45) Date of Patent: Jul. 27, 2021

(54) SYSTEMS AND METHODS FOR SIMULATING HEMODYNAMICALLY RESPONSIVE VASCULATURES

(71) Applicant: The Regents of the University of California, Oakland, CA (US)

(72) Inventors: Benjamin A. Keller, Davis, CA (US); Joseph M. Galante, Davis, CA (US); Anthony J. Carden, Davis, CA (US); Nam K. Tran, Davis, CA (US)

(73) Assignee: The Regents of the University of California, Oakland, CA (US)

( * ) Notice: Subject to any disclaimer, the term of this patent is extended or adjusted under 35 U.S.C. 154(b) by 300 days.

(21) Appl. No.: 16/069,133

(22) PCT Filed: Jan. 11, 2017

(86) PCT No.: PCT/US2017/013047
§ 371 (c)(1),
(2) Date: Jul. 10, 2018

(87) PCT Pub. No.: WO2017/123655
PCT Pub. Date: Jul. 20, 2017

(65) Prior Publication Data
US 2019/0027065 A1    Jan. 24, 2019

Related U.S. Application Data

(60) Provisional application No. 62/277,429, filed on Jan. 11, 2016.

(51) Int. Cl.
*G09B 23/30* (2006.01)
*A61M 5/172* (2006.01)
(Continued)

(52) U.S. Cl.
CPC ........... *G09B 23/303* (2013.01); *A61M 5/142* (2013.01); *A61M 5/168* (2013.01); *A61M 5/172* (2013.01);
(Continued)

(58) Field of Classification Search
CPC ....... G09B 23/28; G09B 23/30; G09B 23/303
See application file for complete search history.

(56) References Cited

U.S. PATENT DOCUMENTS

| | | | | |
|---|---|---|---|---|
| 5,112,228 A | * | 5/1992 | Zouras | G09B 23/285 434/267 |
| 6,062,866 A | * | 5/2000 | Prom | G09B 23/28 434/268 |
| 6,273,728 B1 | * | 8/2001 | van Meurs | G09B 23/28 434/262 |

(Continued)

OTHER PUBLICATIONS

International Search Report and Written Opinion dated Mar. 13, 2017, from application No. PCT/US2017/013047.

*Primary Examiner* — Peter R Egloff
(74) *Attorney, Agent, or Firm* — Foley & Lardner LLP

(57) ABSTRACT

A vasculature simulation device includes an aortic conduit having an inner bore corresponding to a human aorta, a first femoral conduit and a second femoral conduit having an inner bore of a diameter corresponding to a human femoral artery and disposed in fluid communication with the second end of the aortic conduit, and a return conduit in fluid receiving communication with the second end of the aortic conduit. A fluid pump is in fluid receiving communication with the return conduit and is also in fluid providing communication with the first end of the aortic conduit. An access site formed of a penetrable material is disposed adjacent to the first femoral conduit.

21 Claims, 9 Drawing Sheets

(51) Int. Cl.
   *A61M 5/142*    (2006.01)
   *A61M 5/168*    (2006.01)
   *G09B 23/28*    (2006.01)
   *A61B 17/12*    (2006.01)
   *A61B 17/00*    (2006.01)

(52) U.S. Cl.
   CPC ............ *G09B 23/28* (2013.01); *G09B 23/30* (2013.01); *A61B 17/1204* (2013.01); *A61B 17/12109* (2013.01); *A61B 17/12136* (2013.01); *A61B 2017/00716* (2013.01)

(56) References Cited

U.S. PATENT DOCUMENTS

| | | | |
|---|---|---|---|
| 7,413,546 B2 | 8/2008 | Agutter et al. | |
| 8,920,176 B1 | 12/2014 | Yang | |
| 2007/0117077 A1* | 5/2007 | Gordon | G09B 23/28 434/262 |
| 2009/0226867 A1 | 9/2009 | Kalafut et al. | |
| 2009/0246747 A1 | 10/2009 | Buckman, Jr. | |
| 2011/0207105 A1* | 8/2011 | Eggert | G09B 23/281 434/273 |
| 2012/0214144 A1* | 8/2012 | Trotta | G09B 23/32 434/267 |
| 2013/0078604 A1* | 3/2013 | King | G09B 23/30 434/268 |
| 2013/0196301 A1 | 8/2013 | Carson et al. | |
| 2015/0154888 A1* | 6/2015 | Eggert | G09B 23/28 434/268 |
| 2016/0111023 A1* | 4/2016 | Pybus | G09B 23/303 434/268 |
| 2017/0193858 A1* | 7/2017 | Segall | G09B 23/303 |

* cited by examiner

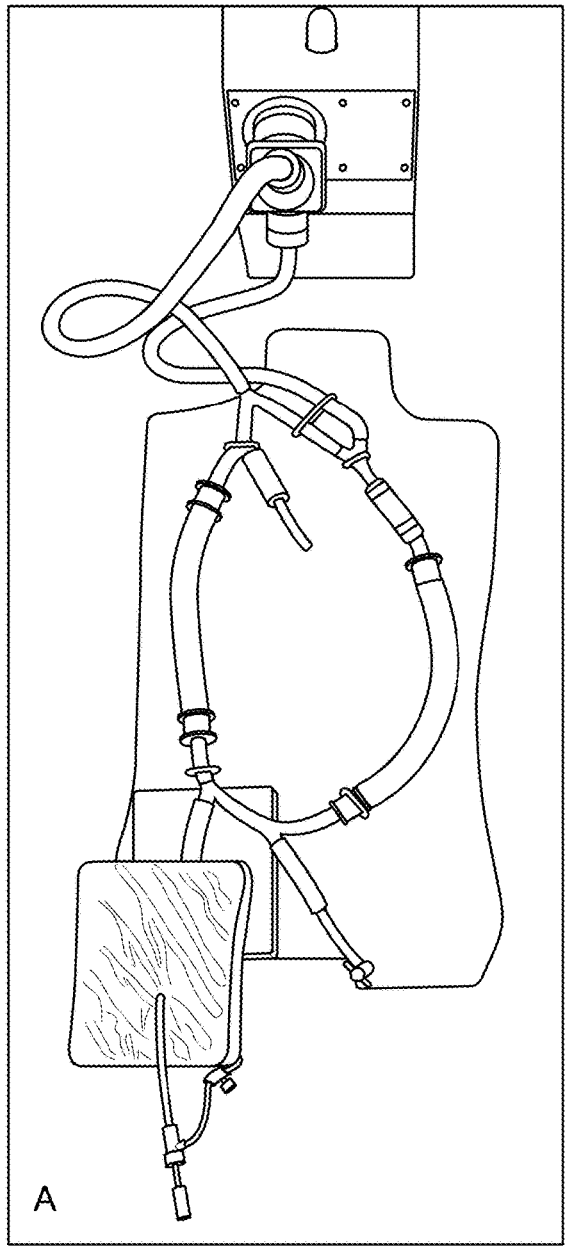
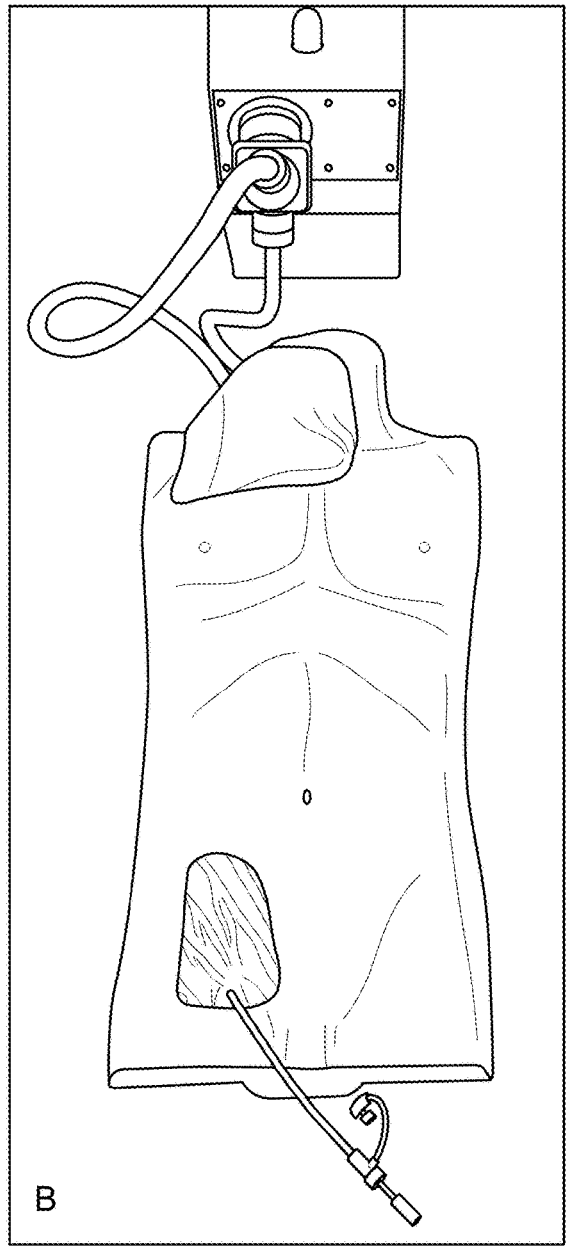
FIG. 5A   FIG. 5B

SYSTEMS AND METHODS FOR SIMULATING HEMODYNAMICALLY RESPONSIVE VASCULATURES

CROSS-REFERENCE TO RELATED APPLICATIONS

This application is a national stage application under 35 U.S.C. § 371 of International Application No. PCT/US2017/013047, filed Jan. 11, 2017, which claims the benefit and priority under 35 U.S.C. § 119(e) of U.S. Provisional Application Serial No. 62/277,429, filed Jan. 11, 2016, the contents of each of which are incorporated by reference herein in their entireties.

BACKGROUND

The use of endovascular interventions for vascular trauma has increased in the past several decades giving trauma surgeons new methods of quickly treating patients with life threatening injuries (Reuben, B. C. et al. (2007) J Vasc Surg. 46(6):1222-1226). Retrograde Endovascular Balloon Occlusion of the Aorta or REBOA was developed to treat non-compressible torso hemorrhage following traumatic injury. This is accomplished by temporary occlusion of the aorta to increase central pressure to the heart and brain while minimizing distal blood loss. After the central pressure has been restored the patient can be transferred to the operating room or endovascular suite for definitive management of their hemorrhage. REBOA is quickly gaining ground as it decreases the morbidity associated with the open resuscitative thoracotomy, which is the more invasive alternative to REBOA in this critically ill patient population (FIGS. 1A-1B).

With increasing interest in REBOA and the overall rarity with which it is performed, several courses have been developed to train physicians on the REBOA technique. This gives physicians familiarity with this rare procedure so when it is needed in an urgent situation, it can be performed without hesitation. The most popular REBOA course is the Basic Endovascular Skills for Trauma (BEST) course (Brenner, M. et al. (2014) J Trauma Acute Care Surg. 77(2):286-291).

SUMMARY

One embodiment of the present disclosure relates to a vasculature simulation device. The device includes an aortic conduit having an inner bore of a diameter corresponding to a human aorta from a first end to a second end. The device further includes a first femoral conduit having an inner bore of a diameter corresponding to a human femoral artery and disposed in fluid communication with the second end of the aortic conduit. The device includes a second femoral conduit having an inner bore of a diameter corresponding to the human femoral artery and disposed in fluid communication with the second end of the aortic conduit. The device further includes a return conduit in fluid receiving communication with the second end of the aortic conduit. The device includes a fluid pump in fluid receiving communication with the return conduit and in fluid providing communication with the first end of the aortic conduit. The device further includes an access site formed of an ultrasound compatible, penetrable material and disposed adjacent to the first femoral conduit.

BRIEF DESCRIPTION OF THE DRAWINGS

FIGS. 5A-5B show the custom vascular platform with reusable foam femoral access, which houses a reusable foam femoral access mold. In FIG. 5B, the simulator has been packaged in a realistic torso with neck and groin cutouts allowing for anatomic landmark identification during simulation sessions.

DETAILED DESCRIPTION

The singular form "a", "an" and "the" include plural references unless the context clearly dictates otherwise. For example, the term "a fluid" includes a plurality of fluids, including mixtures thereof.

Numerical designations and numerical ranges, for example pressure, pH, temperature, time, concentration, and molecular weight, are approximations which are varied (+) or (−) by increments of 0.1. It is to be understood, although not always explicitly stated, that all numerical designations are preceded by the term "about".

The term "comprising" intends that formulations, physical compositions and methods include the recited elements, but do not exclude others. "Consisting essentially of" when used to define systems and methods, shall mean excluding other elements of any essential significance to the combination such as those that do not contribute to the benefit of the claimed embodiments. "Consisting of" shall mean excluding more than trace elements. Embodiments defined by each of these transition terms are within the scope of this disclosure.

Figure 1A:
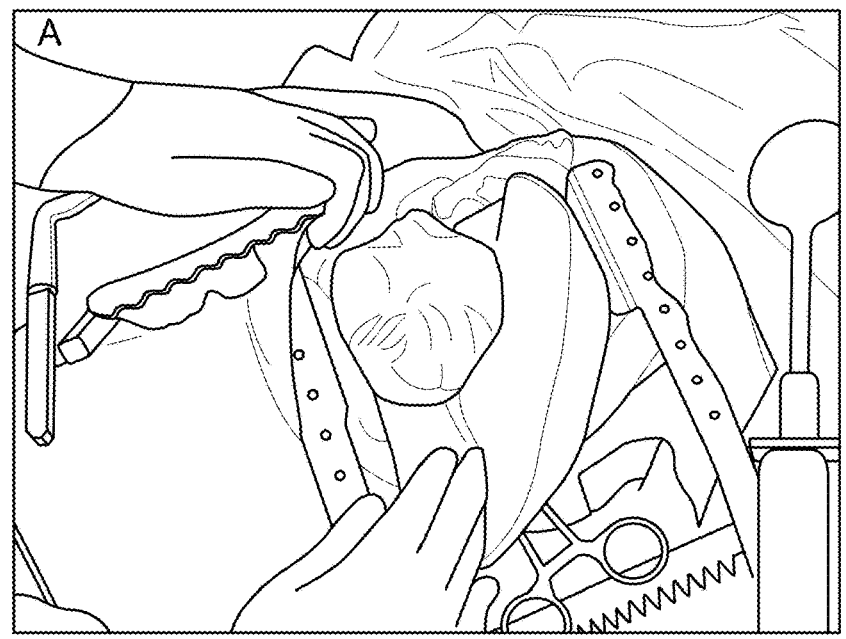
FIGS. 1A-1B show still images demonstrating the invasive nature of a resuscitative thoracotomy which leads to high rates of morbidity (FIG. 1A—Source (Cothren, C. C. et al. (2006) World J Emerg Surg. 1:4)) when compared to REBOA for non-compressible torso hemorrhage (FIG. 1B—Source (Brenner, M. L. et al. (2013) J Trauma Acute Care Surg. 75(3):506-511)).
Figure 1B:
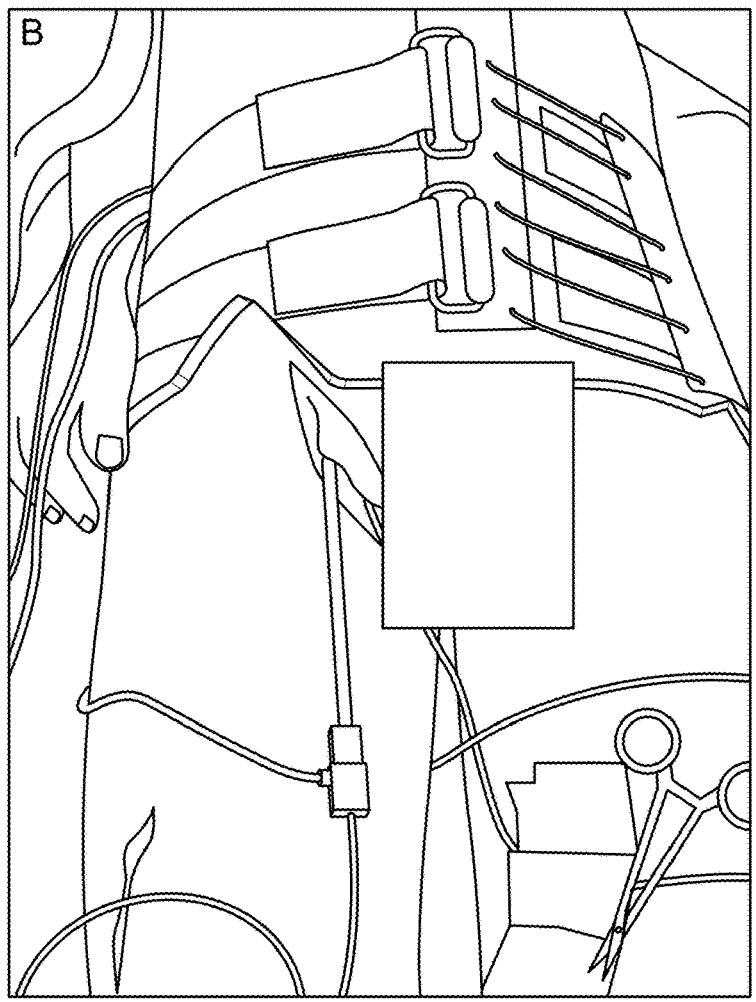
Figure 2:
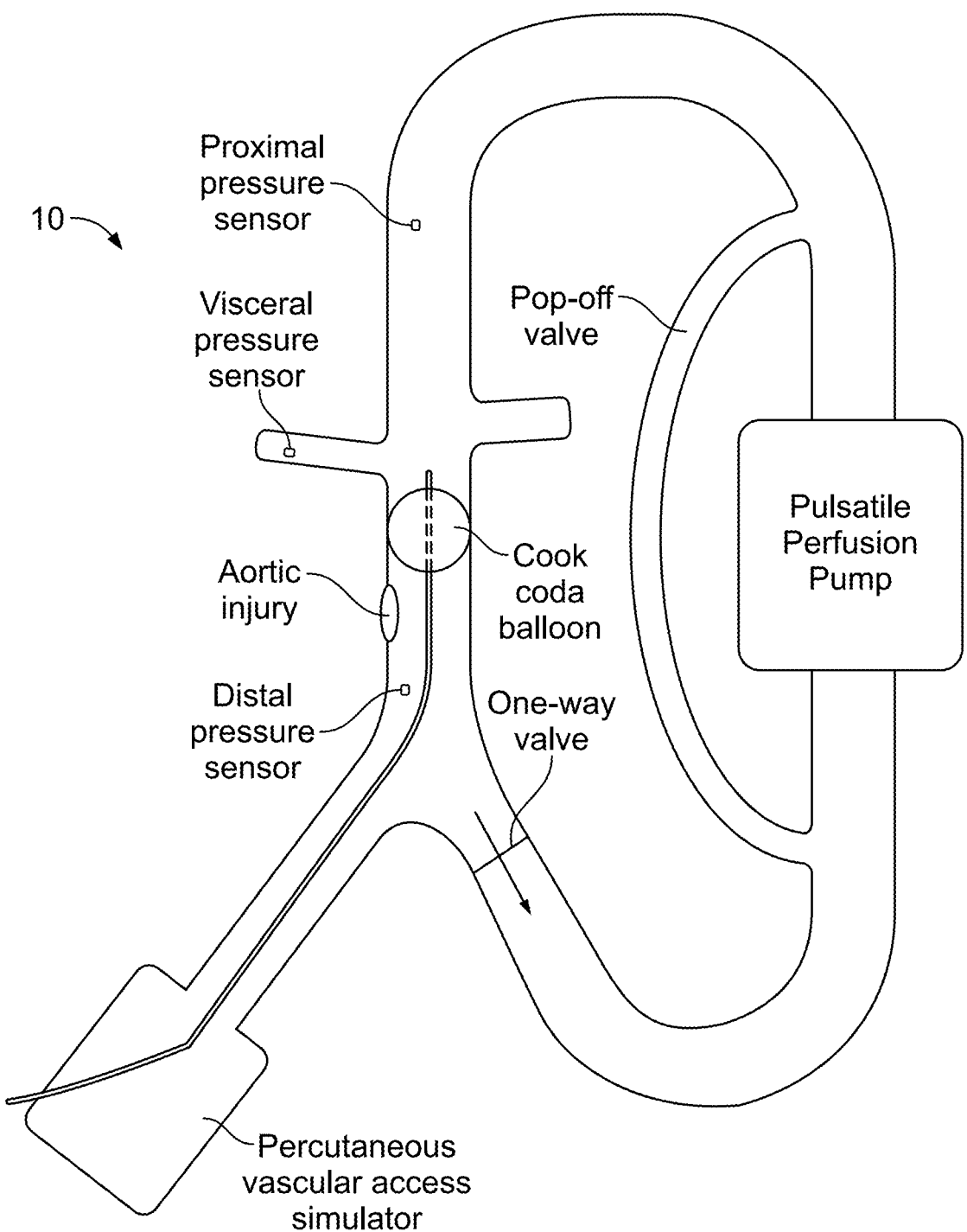
FIGS. 2 and 3 show conceptual designs of vascular circuit simulators.
Figure 3:
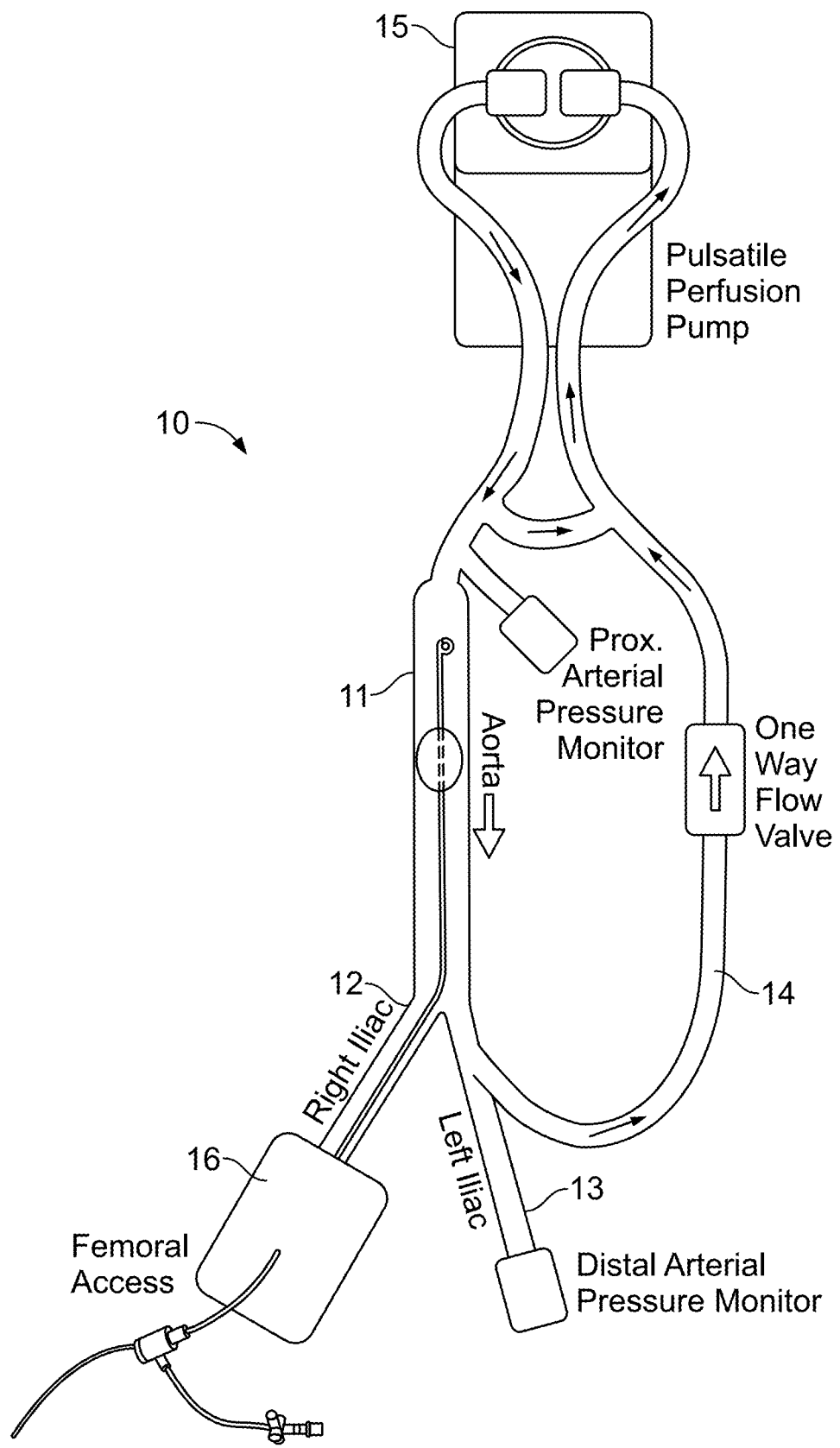
Figure 8:
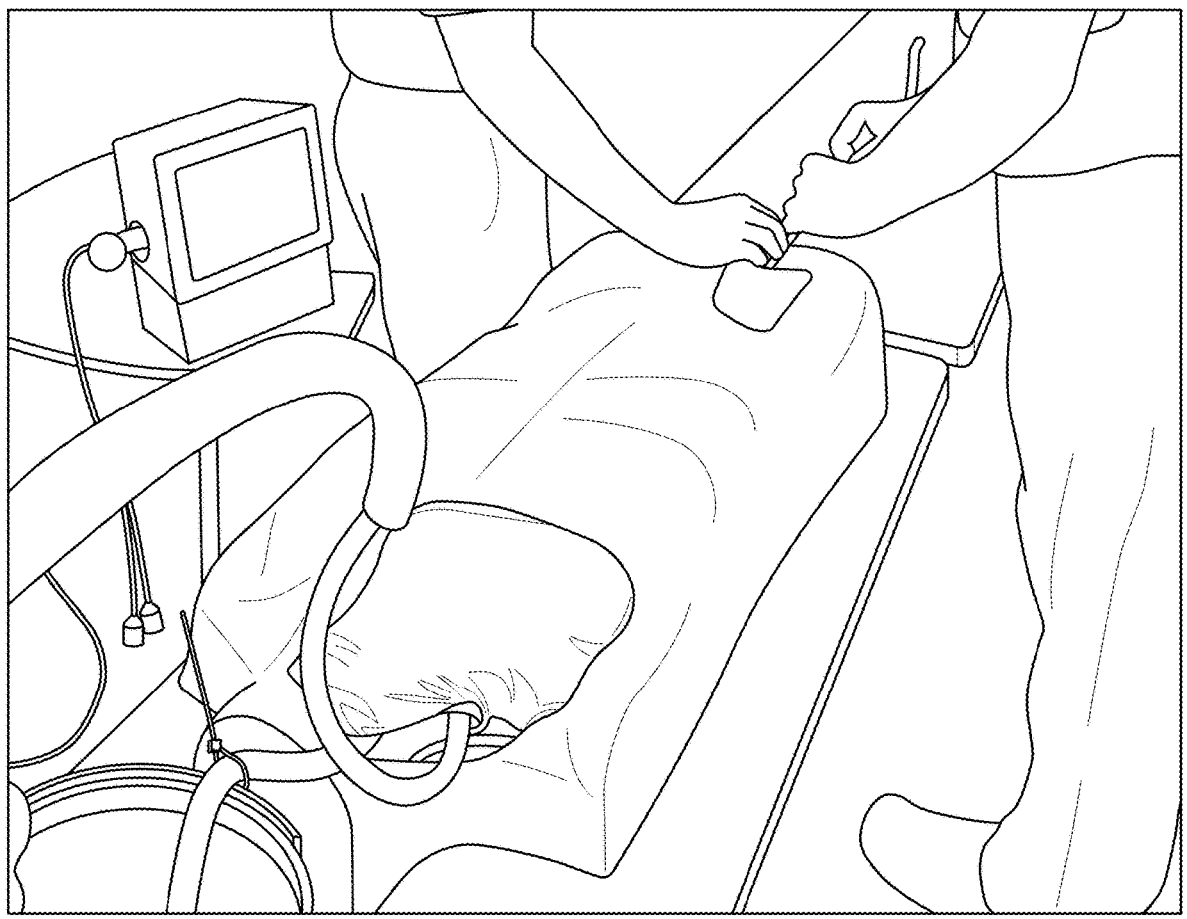
FIG. 8 shows REBOA simulator being used at a UCDMC workshop for the Departments of Trauma and Vascular Surgery in anticipation of starting clinical use of REBOA.
Figure 9A:
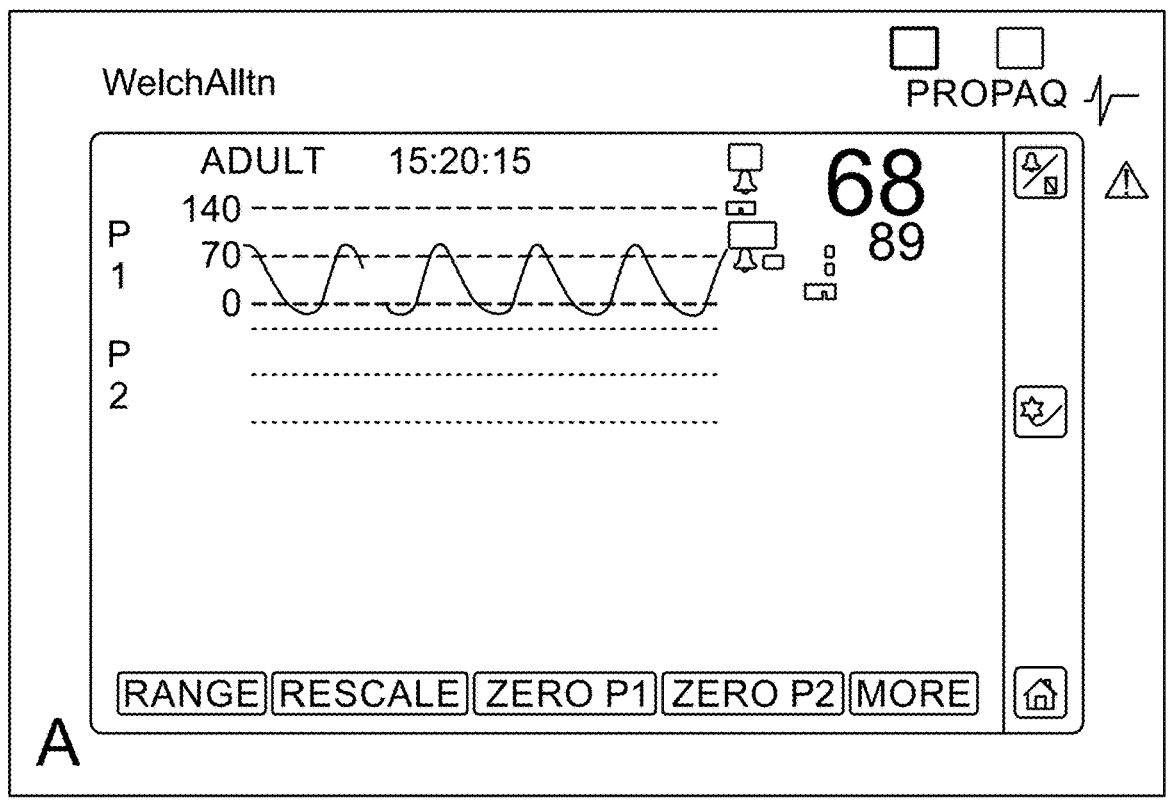
FIGS. 9A-9B show arterial monitors built into the simulator demonstrate an increase in central pressure before (FIG. 6A) and after (FIG. 6B) REBOA deployment.
Figure 9B:
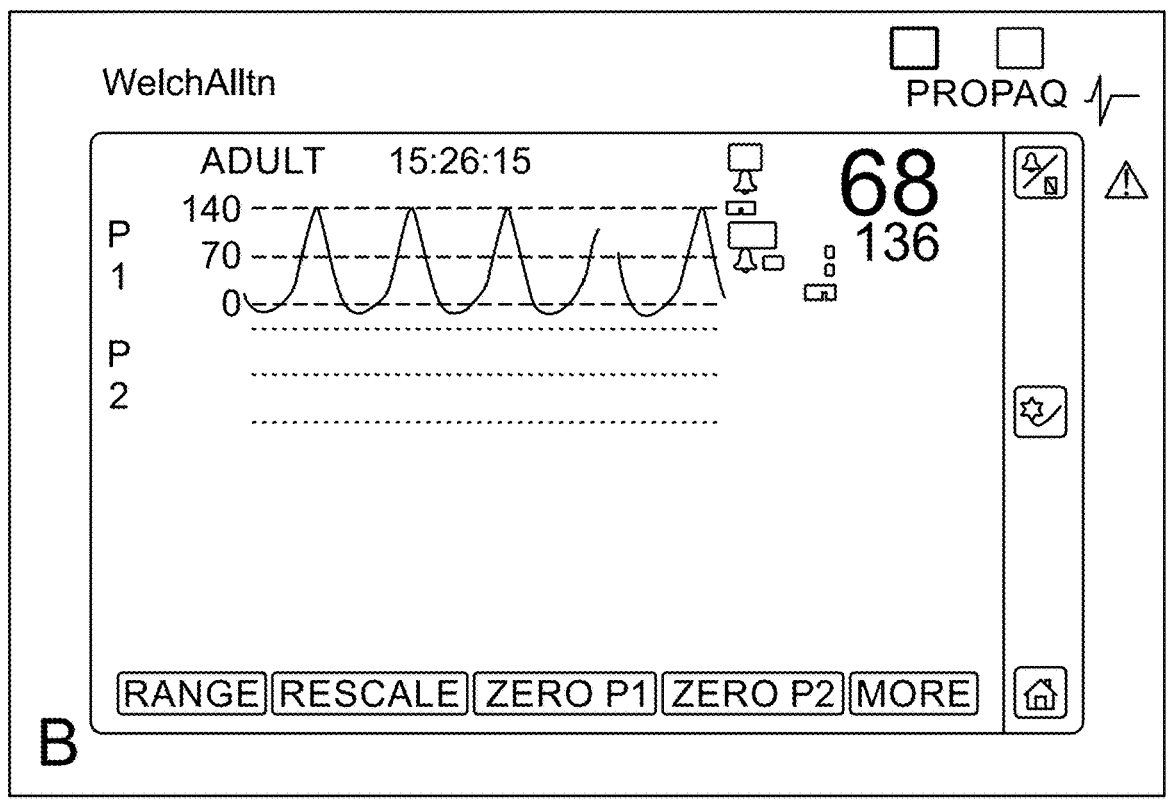

Referring now to FIGS. 2 and 3, system 10 of the present disclosure is a low cost mechanical vasculature simulation device. System 10 may include aortic conduit 11, first femoral conduit 12 in fluid communication with the aortic conduit 11, second femoral 13 conduit in fluid communication with aortic conduit 11, and return conduit 14 in fluid receiving communication with the aortic conduit 11. As shown in FIGS. 2 and 3, the system further includes fluid pump 15 in fluid communication with return conduit 14 and also in fluid communication with aortic conduit 11. Access site 16 is disposed adjacent to first femoral conduit 12 and provides access to first femoral conduit 12. Access site 16 may be made of penetrable material such as gelatin or foam and may also be ultrasound compatible. System 10 may further include monitors, e.g. arterial monitors, and computing devices built into the simulator as shown in FIGS. 8, 9A and 9B. These monitors and computing devices may be used to process data from sensors incorporated into the system and may display information such as cardiac output, systolic blood pressure, diastolic blood pressure and heart rate, among other things.

As is shown in FIG. 3, the vascular circuit resulting from system 10 may be completed with additional latex tubing that branches off the left femoral artery and returns to the perfusion pump. A one-way check valve in the return tubing and a proximal circuit shunt may prevent retrograde flow within the circuit and shunts antegrade flow during periods of occlusion respectively.

Utilizing a pulsatile perfusion pump and simple vascular circuit, a hemodynamically responsive endovascular simulator was created capable of simulating human vascular anatomy with near physiologic parameters. This low cost, high fidelity simulator is useful for training health care providers in both simple and complex endovascular procedures, including REBOA as well as for the testing and development of new endovascular devices. The simulator described herein optimizes the characteristics needed to train providers to perform the procedure and can be used as an alternative, or in addition to, virtual reality simulators, animal models, and perfused cadavers. The simulators described herein provide many beneficial features which may include:

1. Physiologic Hemodynamic Properties: This endovascular simulator may be capable of producing physiologic hemodynamics. This makes it useful for education training as the hemodynamic parameters produced by simulator (e.g., simulated heart rates and simulated blood pressures) and displayed on the arterial monitoring systems are easily translated to clinical situations. The simulator may be adjusted to mimic a hypotensive trauma patient and interventions can augment the hemodynamics to demonstrate a therapeutic outcome. In addition to accuracy for physician training, the physiologic hemodynamic properties allow the simulator to test endovascular devices to see how they behave in a simulated environment before transitioning testing to pre-clinical and clinical environments.

2. Femoral Vascular Access: The femoral access site for the simulator may be created from penetrable materials such as a re-usable gelatin based mold that is ultrasound compatible but also transmits pulsations from a pulsatile pump. This allows for the simulation of both ultrasound guided access and access guided by tactile palpation of the femoral pulse.

3. Haptic Feedback: The pulsatile perfusion and vascular circuit allow for life-like haptic feedback unlike current computer based simulators. Inflating a balloon catheter within the endovascular simulator gives those training on this mechanical based simulator much more realistic feel resulting in improved training.

4. Complication Simulation: There are several complications that can be easily simulated including complications from vascular access injuries, inappropriate catheter placement in aortic branches and incomplete REBOA placement.

5. Dynamic Balloon Visualization: The simulator's simple circuit can be made out of fluid conduits formed from visually transparent materials (e.g., transparent or semi-transparent plastic tubing). This allows users to visualize the placement of catheters and balloon deployment during simulation scenarios. Those who are training on the model may verify that they have positioned catheters, wires, and balloons in the correct location based on the clinical scenario further enriching the training aspect. In addition, having a see through circuit allows for those testing and designing new endovascular devices to monitor flow dynamics during testing of the prototype equipment making it easier for developers to refine their device before using them in pre-clinical studies.

6. Low Cost: Existing REBOA endovascular simulators on the market cost over $80,000. Given the simple vascular circuit and lack of an integrated computer system, the cost can be minimized.

Existing simulators on the market (e.g., Mentice, Simbionix) are computer based simulators and not based off of a mechanical pulsatile perfusion system. While computer simulation can replicate clinical scenarios, it does not provide the same haptic feedback that this endovascular pulsatile perfusion simulator does. This gives users a more realistic simulation experience.

In addition to existing computer based simulators, perfused cadavers are utilized for some endovascular training courses. While anatomically correct, perfused cadavers carry the risk bio hazardous occupational exposures to trainees. Perfused cadavers are also expensive and are not reusable like the proposed hemodynamically responsive endovascular simulator for REBOA training making it a more affordable option for simulation.

Hemodynamically Adjustable Model (HAM) for REBOA Simulation

REBOA is an alternative to resuscitative thoracotomy in patients with non-compressible torso hemorrhage. Utilization of endovascular techniques for traumatic arterial injuries has increased with sixteen percent of vascular injuries being managed endovascularly (Avery, L. E. et al. (2012) J Trauma Acute Care Surg. 72(1):41-46, discussion 46-47). Realistic simulation is required for REBOA skill acquisition so it can be employed quickly and without hesitation in critically ill patients (Brenner, M. et al. (2014) J Trauma Acute Care Surg. 77(2):286-291; Villamaria, C. Y. et al. (2014) J Trauma Acute Care Surg. 76(4):929-935, discussion 935-936).

Resuscitative endovascular balloon occlusion of the aorta (REBOA) is an adjunct technique to salvage patients with non-compressible torso hemorrhage. Current REBOA training paradigms require large animals or human cadavers for acquisition of skills. This adds cost and logistical obstacles to training that may prevent widespread dissemination of REBOA. Applicants' low-cost, near-physiologic REBOA simulator may replace the need for costly animal models. The low-cost REBOA simulator permits near physiologic, pulsatile perfusion for physician training and endovascular device development as an alternative to costly computer based endovascular simulators and animal models.

Figure 4:
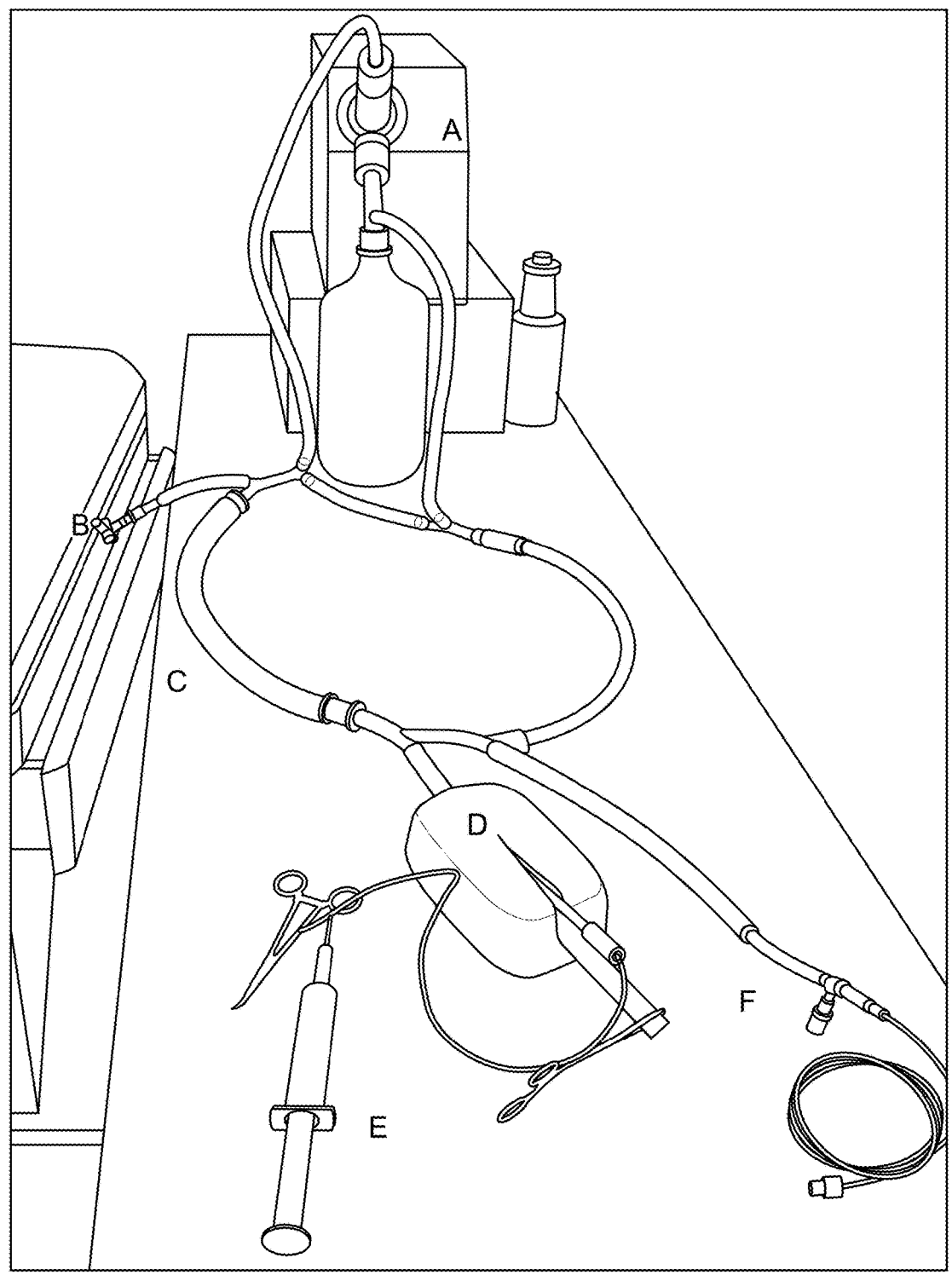
FIG. 4 shows an example arrangement of the REBOA simulator including: (A) Perfusion pump, (B) Proximal arterial monitor, (C) Aorta, (D) Right femoral artery with gelatin puncture site, (E) REBOA balloon Catheter, and (F) Left femoral artery with distal arterial monitor.

One embodiment of system 10 is a Retrograde endovascular balloon occlusion of the aorta (REBOA) simulator, such as the one illustrated in FIGS. 4 and 5. While FIG. 5 a gelatin mold is used in FIG. 4, FIG. 5 illustrates a simulated vascular circuit with the reusable foam femoral access mold. Also, in FIG. 5, the simulator has been packaged into a realistic torso for anatomic landmark identification. As illustrated in these figures, balloon, inflation at the level of the xyphoid simulates zone one deployment (between the left subclavian artery and celiac artery), while placement at the level of the umbilicus simulates zone 3 deployment (between the lowest renal artery and aortic bifurcation).

As is illustrated in FIGS. 4 and 5 REBOA simulator may achieve pulsatile perfusion by using a perfusion pump, e.g., Harvard Apparatus pump, and the anatomic vascular circuit may be constructed out of latex, vinyl and/or PVC tubing. Retrograde balloon occlusion may be achieved using a Cook Coda balloon catheter. Pressure sensors may be placed in conduits corresponding to the proximal aorta and distal iliac artery to obtain pressure monitoring and arterial tracings, as is illustrated in FIGS. 2 and 3. Vascular circuit constructed using latex and vinyl conduits to mimic aorta, iliac bifurcation, and femoral arteries. Pulsatile fluid flow established using a programmable perfusion pump. Hemodynamic properties may be evaluated using arterial monitors in the proximal and distal aorta, as illustrated in FIGS. 9A and 9B. REBOA may be achieved using a Cook CODA balloon catheter through a 12 Fr sheath. Furthermore, One Way Check Flow Valve, Couplers and Stopcocks may be utilized in the models described herein.

An exemplary pulsatile simulator capable of generating cardiac outputs ranging from 1.7-4.5 liters per minute with corresponding arterial pressures of 89-184/65-121 mm Hg was successfully tested. The simulator shown in FIG. 8 was assessed at a REBOA workshop for the UCDMC Trauma and Vascular Surgery Departments. The simulator accommodates an introducer sheath compatible with the Coda balloon catheter. Upon inflation of the REBOA catheter, the arterial waveform distal to the occlusion flattens and distal pulsation within the simulator is lost. Systolic pressures proximal to the inflated occlusion balloon may increase by as much as 62 mm Hg, simulating the ability to increase proximal perfusion when the catheter is deployed. A low cost pulsatile REBOA simulator was developed. Applicants' simulator is low cost compared to conventional systems. The REBOA simulator may be capable of producing near physiologic hemodynamics (Table 2 below). Adjusting the heart rate and stroke volume on the pulsatile perfusion pump allows for recreation of clinical scenarios. Upon REBOA deployment, arterial pressure monitors demonstrate an increase in central pressure proximal to the balloon and an absence of perfusion distal to the balloon (FIGS. 9A-9B). The simulator may be used as a training tool and is able to effectively teach the steps of REBOA, demonstrate a therapeutic benefit when the CODA catheter is deployed in the correct location, and provide realistic haptic feedback for the user (FIG. 8).

Applicants have designed a cost effective simulator capable of producing near physiologic blood pressure and flow dynamics that respond in real time to balloon catheter manipulation. The simulator may permit refinement, reduction, and replacement of large animal models for training purposes, facilitating lower cost, high fidelity simulation and widespread application of REBOA. A low-cost, high fidelity REBOA simulator utilizing a simple vascular circuit and pulsatile perfusion pump is provided herein. Manipulating pump settings can allow for near physiologic hemodynamics and replication of clinical scenarios for training sessions.

The simulator may further include built-in simulated complications relating to femoral access and inappropriate REBOA deployment. The simulator may be used to train surgical residents to perform the REBOA procedure and to test and enhance new endovascular devices related to REBOA.

The Hemodynamically Responsive Simulator for Retrograde Endovascular Balloon Occlusion of the Aorta or REBOA Simulator may fit the needs of both trainees and device developers by leveraging a physiologic pulsatile perfusion system. FIG. 2 illustrates a circuit including a pump, e.g., a pulsatile perfusion pump, that may be incorporated in the hemodynamically responsive simulator. A simulator may further use latex and tubing, e.g., vinyl tubing, with such a circuit.

Anatomic Circuit

The anatomic vascular circuit may be constructed to simulate an abdominal aorta that Y's into bilateral femoral arteries. The simulated right femoral artery conduit may be used as the vascular puncture site and provides access to the simulator via a gelatin puncture mold or foam mold. As shown in FIGS. 2 and 3 and discussed above, the Anatomic circuit may comprise aortic conduit 11, first femoral conduit 12, second femoral conduit 13, return conduit 14, fluid pump 15 and access site 16. The conduits may be made from latex tubing. The pump inflow and outflow may be made of 1.3-cm ID polyvinyl chloride tubing. Polymer connectors in the circuit allow for transitions between different size tubing and branches/bifurcations within the circuit.

The left femoral artery conduit including a selectable fluid valve may be used for simulating hemorrhage in the model and for distal pressure monitoring via an arterial line set up. The circuit may be completed with a return conduit that Y's off the left femoral artery conduit returning the circulating fluid back to the pulsatile perfusion pump. This closed circuit minimized the need to add fluid to the simulator over a training day. There may be a one-way flow check valve in the return tubing to prevent retrograde flow within the circuit. An additional arterial pressure transducer may be built into the simulator proximal to the aorta conduit to monitor proximal pressure in the system and to demonstrate a therapeutic effect when an endovascular intervention (e.g., REBOA balloon inflation) is performed.

Circuit Sizing

The tubing sizes for the aorta and femoral artery conduits may be chosen based on anatomic literature previously published for the average sizes of these corresponding vessels in adults. The normal aorta measures approximately 3 cm in the chest and upper abdomen and tapers to 2 cm in the lower abdomen just before the bifurcation of the aorta (O'Gara, P. T. (2003) Circulation 107(6):e43-e45).

Based on this a latex tube with an inner bore having a 2.5 cm inner diameter may be used for the aorta. The average femoral artery size in normal adults is approximately 1.0 cm in size and therefore latex tubing with an inner bore having a 1.3 cm inner diameter size may be used (Sandgren, T. et al. (1999) J Vasc Surg. 29(3):503-510). The conduits may be latex tubing. These dimensions reflect the aortic and common femoral artery diameters in healthy adults.

Femoral Access

Figure 6B:
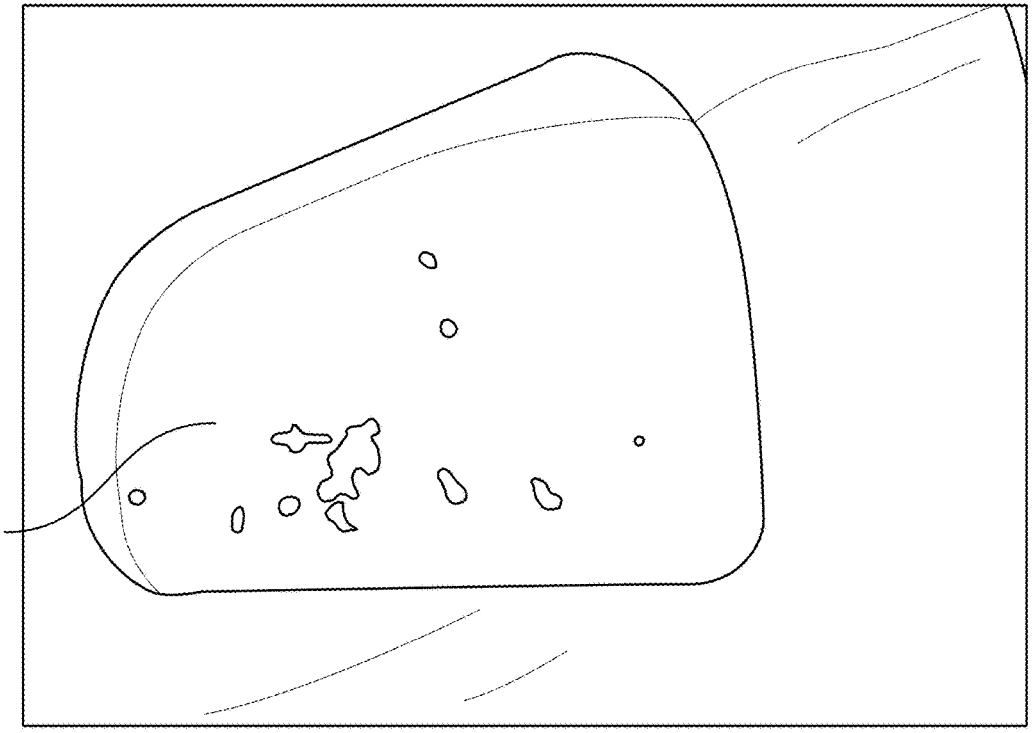
FIGS. 6A-6B show groin cutouts housing a foam mold (FIG. 6A) and a gelatin mold (FIG. 6B).
Figure 6A:
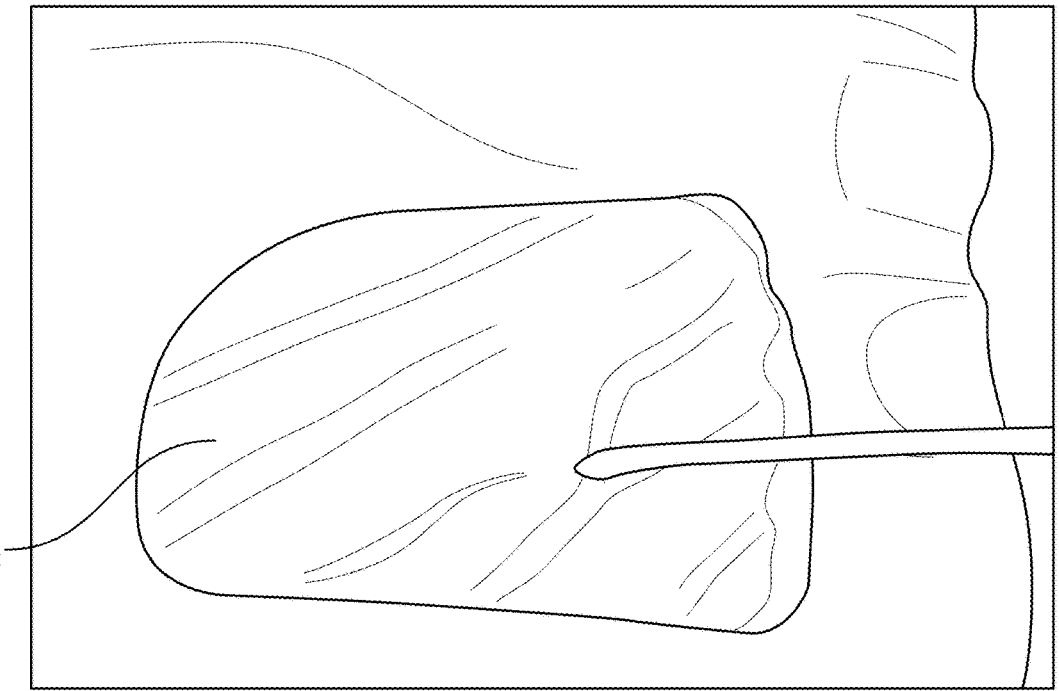

The femoral artery is one of the standard sites for endovascular arterial access and is a site for REBOA access given the vascular size requirements needed to accommodate a large diameter (12Fr.) sheath. Referring now to FIGS. 6A and 6B, a femoral access site may be created out of foam mold 21, as shown in FIG. 6A, or gelatin mold 22, as shown in FIG. 6B. Foam mold 21 may be customizable and interchangeable. Also, foam mold 21 is more durable than the gelatin mold 22 and may be used, however foam mold 21 may not be ultrasound compatible. The foam mold 21 may be used for REBOA training with the sheath in place but may not be intended for vascular access training like the gelatin mold. As such, foam mold 21 with a 12. Fr sheath (Cook Medical, Bloomington, Ind.) already in place allows trainees to focus on REBOA deployment alone without having to gain arterial access.

Figure 7:
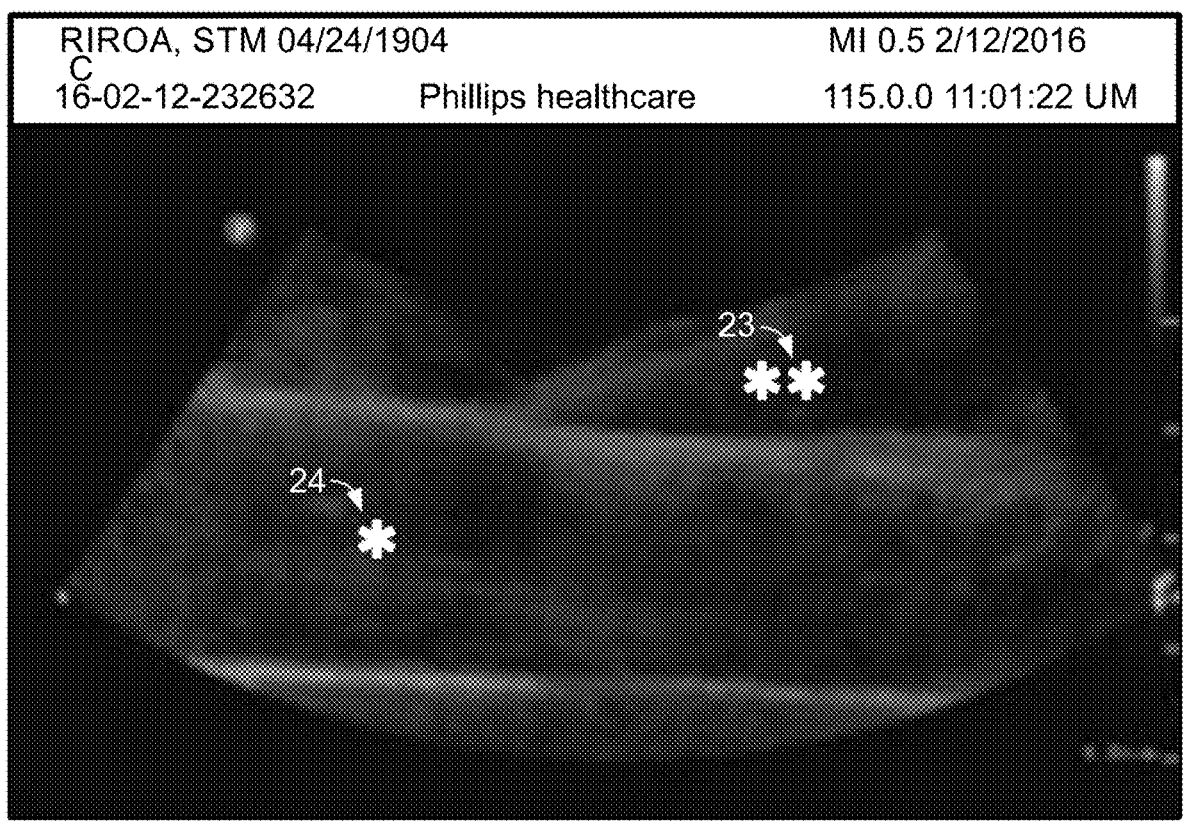
FIG. 7 shows an ultrasound image taken of a needle penetrating a gelatin mold.

Gelatin mold 22, is less durable than foam mold 21 but is ultrasound compatible as is illustrated in FIG. 7. As such gelatin mold 22 allows for ultrasound-guided vascular access. FIG. 7 shows an ultrasound image taken of a needle penetrating gelatin mold 22. As is shown in FIG. 7, needle track 23 is visually identifiable as is needle tip 24. In addition, gelatin mold 22 transmits pulsations generated from the perfusion pump allowing for anatomic, tactile pulse guided arterial access. Additional replacement gelatin molds will be a consumable that can be purchased as needed.

Pulsatile Perfusion

Pulsatile perfusion may be created in the anatomic circuit using a perfusion pump, e.g., Harvard Apparatus Pulsatile Blood Pump for Large Animals and Hemodynamic Studies (Model #1423). While this is the pump that is used in FIG. 8, it can easily be exchanged for another perfusion pump. The perfusion pump may allow for adjustment in heart rate (30-80 beats/min) and stroke volume (15-100 mL/stroke). This allows for the user to dial in certain hemodynamics to simulate different clinical settings (e.g., simulated heart rates and simulated blood pressures). Specifically, The stroke volume and pump rate can be adjusted to recreate clinical scenarios such as a hypotensive trauma patient. The circuit is primed with water and purged of air via integrated three-way stopcocks. The pump has been integrated into the circuit with inflow and outflow conduits. This allows for a completed circuit so once the pump and circuit are primed there may not be a need to add additional fluid (e.g., water) to the simulator. The pump, anatomic circuit and gelatin or foam access mold may complete the working components of the simulator (FIG. 3).

Integrated Invasive Pressure Monitoring

As is illustrated in FIGS. 2 and 3, two arterial blood pressure transducers may be integrated into the system with one transducer located in the proximal aorta and the second transducer in the left femoral artery. These pressure transducers may be connected to commercially available invasive blood pressure monitors to provide real-time pressure tracings for determining correct REBOA deployment with an augmented pressure proximal to the REBOA balloon and an absence of arterial pressure distally.

Simulator Housing

The refined vascular circuit may be housed in a torso model to improve the realism of the simulator and provide anatomic landmarks to assist with training modules, as shown in FIGS. 5A, 5B and 8. As shown in FIG. 5A, the circuit may be laid out on a custom designed platform that allows for easy manipulation and modification of the circuit to meet the users' needs (tubing changes). The torso may lift off the vascular platform giving trainees and device designers the ability to visualize balloon placement to confirm the appropriate intervention has been performed for the specific clinical situation. The torso may include a cutout in the neck that is used to connect the simulator to the pulsatile perfusion pump. A second cutout in the right groin allows for catheter based access via the custom made gelatin or foam femoral access molds.

Simulator Deployment and Testing

To gain access to the simulator, percutaneous cannulation of the right common femoral artery using an arterial catheter is performed. Correct placement is confirmed via pulsatile flow through the access needle and via ultrasound. For example, using the Seldinger technique, a 0.035-inch Amplatz wire may be placed into the arterial catheter, and the catheter may be upsized to a 12 Fr sheath. Subsequently, a 12 Fr 32-mm CODA balloon catheter may be placed over the wire and advanced to simulate either Zone one or three occlusions. The CODA balloon may then be inflated, and with the use the integrated arterial monitors and haptic feedback provided by the simulator, a therapeutic response may be observed. Correct anatomic placement of the balloon catheter within the intended zone may be confirmed by lifting up the simulated torso and palpating the balloon within the aorta.

After REBOA has been performed, the balloon can be deflated and removed. The sheath can be removed, and the procedure can be repeated up to four times using the same gelatin groin mold before a new mold is required. Using the foam mold with the sheath already in place allows for an unlimited number of REBOA deployments during a training session.

Performance and Results

The REBOA simulator, shown being tested in FIG. 8, has been run through several phases of testing including both hemodynamic testing and internal UCDMC REBOA simulation workshops. These tests have highlighted the usefulness of the simulator and how close it comes to mimicking clinical situations. The benefits over the alternatives discussed above are evident in Table 1 below:

TABLE 1

Direct Comparison of the Perfused Cadaver Model, Virtual Reality (VR) Simulators, and Animal Training Models to our Pulsatile Perfusion Simulator

| | Training Model | | | |
|---|---|---|---|---|
| | Perfused Cadaver | VR simulator | Animal model | Pulsatile simulator |
| Cost | High | High | High | Low |
| Portable | No | Variable | No | Yes |
| Reusable | No | Yes | No | Yes |
| Anatomical Accuracy | Yes | No | No | Yes |
| Haptic Feedback | Yes | Variable | Yes | Yes |
| Dedicated Facility | Yes | No | Yes | No |
| Ethical Concerns | Yes | No | Yes | No |
| Occupational Exposure | Yes | No | Yes | No |

Hemodynamic Testing

The pulsatile perfusion pump and the vascular circuit are capable of producing near physiologic simulated hemodynamics for cardiac output, heart rate, and blood pressure (Table 2 below). The simulated heart rate and blood pressure parameters may be captured through the proximal and distal arterial monitors and displayed in real time on a propaq displays. With manipulations of the pump settings, clinical scenarios can be recreated to simulate a hypotensive patient. Interventions on the simulator can also be tracked in real time to demonstrate a therapeutic effect. For example, inflation of a REBOA catheter in the aorta can increase the proximal perfusion pressures by up to 62 mm Hg and result in absence of perfusion distal to the inflated REBOA balloon.

Testing has shown that the pump is capable of a simulated cardiac output of 1.7 to 6.8 L/minute. Using the integrated arterial monitors, the circuit and pump are capable of generating systolic blood pressures (SBP) of 54 to 226 mmHg and diastolic pressures of 14 to 121 mmHg (Table 2). With REBOA deployment, an increase in the proximal SBP can be titrated based on the degree of balloon inflation with pressure improvements of 10 to 62 mmHg. In addition to an improvement in proximal pressures, the distal arterial waveform dampens, the SBP drops to 0 mmHg, and a lack of distal pulses on the simulator can be observed.

TABLE 2

Hemodynamic Properties Generated by the REBOA Simulator

| Hemodynamic Parameter | Minimal Value | Maximal Value |
|---|---|---|
| Cardiac Output (L/min) | 1.7 | 6.8 |
| Systolic Blood Pressure (mm Hg) | 54 | 226 |
| Diastolic Blood Pressure (mm Hg) | 14 | 121 |
| Heart Rate (beat/min) | 30 | 80 |
| Systolic Therapeutic Response (mm Hg) | 10 | 62 |

Simulation Workshop

As a proof of concept, the simulator was used at an internal REBOA training workshop for the University of California, Davis Medical Center trauma and vascular surgeons, shown in FIG. 9. The feedback on the simulator was positive and several commented on the realistic haptic feedback, which is an essential part of training the REBOA procedure.

The mechanical based endovascular simulator may use pulsatile perfusion to recreate physiologic hemodynamics for both REBOA training and device development. The simulator described above has several elements that need not be built into other current computer based endovascular simulators and does it for a fraction of the cost. By using pulsatile perfusion, this simulator is more realistic and provides superior haptic feedback giving users a more accurate training environment.

REFERENCES

1. Dawson, D. L. et al., Training with simulation improves residents' endovascular procedure skills. J Vasc Surg, 2007. 45(1): p. 149-54.
2. Methods and apparatus for simulation of endovascular and endoluminal procedures, WO2006020792A2, Publication date Feb. 23, 2006.
3. Endovascular surgery simulator with hemodynamic function, WO2013040195A3, Publication date Jul. 25, 2013.

It is to be understood that while this disclosure has been described in conjunction with the above embodiments, that the foregoing description and examples are intended to illustrate and not limit the scope of the disclosure. Other aspects, advantages and modifications within the scope of this disclosure will be apparent to those skilled in the art to which the disclosure pertains.

What is claimed is:

1. A vasculature simulation device comprising:
an aortic conduit having an inner bore of a diameter corresponding to a human aorta from a first end to a second end;
a first femoral conduit having an inner bore of a diameter corresponding to a human femoral artery and disposed in fluid communication with the second end of the aortic conduit;
a second femoral conduit having an inner bore of a diameter corresponding to the human femoral artery and disposed in fluid communication with the second end of the aortic conduit;
a return conduit in fluid receiving communication with the second femoral conduit;
a fluid pump in fluid receiving communication with the return conduit and in fluid providing communication with the first end of the aortic conduit;
a shunt having a first end coupled to the aortic conduit downstream of the fluid pump, and a second end coupled to the return conduit upstream of the fluid pump; and
an access site formed of a penetrable material and disposed adjacent to the first femoral conduit.

2. The device of claim 1, wherein the fluid pump is configured to deliver a pulsatile fluid flow into the first end of the aortic conduit.

3. The device of claim 2, wherein the access site is formed of reusable foam.

4. The device of claim 2, wherein the access site is formed of ultrasound compatible gelatin.

5. The device of claim 2, wherein the access site is formed to allow tactile detection of the pulsatile fluid flow.

6. The device of claim 2, further comprising a first arterial monitor disposed toward the first end of the aortic conduit and configured to measure at least one of a simulated heart rate and a simulated blood pressure.

7. The device of claim 2, further comprising a second arterial monitor disposed at the second femoral conduit and configured to measure at least one of a simulated heart rate and a simulated blood pressure.

8. The device of claim 1, wherein the second femoral conduit includes a fluid valve configured to selectively allow fluid to flow through the second femoral conduit and out of the device.

9. The device of claim 1, wherein the return conduit includes a one-way valve configured to prevent fluid from flowing through the return conduit toward the aortic conduit.

10. The device of claim 1, wherein the diameter of the inner bore of the aortic conduit tapers from the first end to the second end.

11. The device of claim 1, wherein each of the first femoral conduit and the aortic conduit is formed of a visually transparent material.

12. The device of claim 1, wherein at least some of the vasculature simulation device is disposed within a housing formed to imitate landmarks on a human body.

13. The device of claim 11, wherein the landmarks include a neck and a groin, and wherein the access site is disposed at the groin.

14. A method of using the vasculature simulation device of claim 1, the method comprising using the vasculature simulation device to simulate an intravascular procedure.

15. A method for simulating a human's vasculature, the method comprising:
selecting a vasculature simulation device comprising:
an aortic conduit having an inner bore of a diameter corresponding to a human aorta from a first end to a second end;
a first femoral conduit having an inner bore of a diameter corresponding to a human femoral artery and disposed in fluid communication with the second end of the aortic conduit;
a second femoral conduit having an inner bore of a diameter corresponding to the human femoral artery and disposed in fluid communication with the second end of the aortic conduit;
a return conduit in fluid receiving communication with the second femoral conduit;
a fluid pump in fluid receiving communication with the return conduit and in fluid providing communication with the first end of the aortic conduit;

a shunt having a first end couple the aortic conduit downstream of the fluid pump, and a second end coupled to the return conduit upstream of the fluid pump; and an access site formed of a penetrable material and disposed adjacent to the first femoral conduit; and pumping fluid in the vasculature simulation device using the fluid pump.

16. The method of claim 15, wherein pumping the fluid comprises delivering a pulsatile fluid flow.

17. The method of claim 16, wherein delivering the pulsatile fluid flow comprises delivering the pulsatile fluid flow into the first end of the aortic conduit.

18. The method of claim 16, wherein the access site is formed of at least one of reusable foam or ultrasound compatible gelatin and to allow tactile detection of the pulsatile fluid flow.

19. The method of claim 15, further comprising puncturing the access site.

20. The method of claim 15, further comprising measuring simulated heart rate in the vasculature simulation device.

21. The method of claim 15, further comprising measuring simulated blood pressure in the vasculature simulation device.

* * * * *